United States Patent [19]
Timberlake et al.

[11] Patent Number: 5,756,305
[45] Date of Patent: May 26, 1998

[54] IDENTIFICATION OF ESSENTIAL SURVIVAL GENES

[75] Inventors: William Timberlake, Bolton; Victoria Gavrias, Watertown, both of Mass.

[73] Assignee: Millennium Pharmaceuticals, Inc., Cambridge, Mass.

[21] Appl. No.: 643,591

[22] Filed: May 6, 1996

[51] Int. Cl.$^6$ .............. C12Q 1/04; C12N 1/14; C12N 1/20; C12N 15/01

[52] U.S. Cl. .............. 435/34; 435/29; 435/172.1; 435/252.1; 435/252.8; 435/253.4; 435/254.1; 435/255.1

[58] Field of Search .............. 435/69.1, 172.1, 435/172.3, 252.1, 252.33, 252.35, 254.1, 254.11, 254.2, 254.3, 29, 34, 252.8, 252.4, 255.1

[56] References Cited

PUBLICATIONS

Lodge et al., "Comparison of Myristoyl–CoA:Protein N–Myristoyltransferases from Three Pathogenic Fungi: *Cryptococcus neoformans*, *Histoplasma capsulatum*, and *Candida albicans*," J. Biol. Chem. 28:2996–3009, 1994.

Schmid et al., "Genetic Analysis of Temperature–Sensitive Lethal Mutants of *Salmonella typhimurium*," Genetics, 123:625–633, 1989.

Smith et al., "Hyphal Tip Extension in *Aspergillus nidulans* Requires the manA Gene Which Encodes Phosphomannose Isomerase," Mol. and Cell. Biol., 14:6030–6038, 1994.

van Zyl et al., "A General Screen for Mutants of *Saccharomyces cerevisiae* Deficient in tRNA Biosynthesis," Genetics, 123:55–68, 1989.

Winston, "Mutagenesis of Yeast Cells," *Current Protocols in Molecular Biology*, Supplement 19, 2:13.3.1–13.3.4, 1992.

Inoko et al. "Isolation & Characterization of Conditional–Lethal Rho Mutants of *Eschericia coli*" DNAS 74(3) 1162–1166, Mar. 1977.

Hou et al. "In Vivo Selection of Conditional–Lethal Mutations in the Gene Ecoding Elongation Factor F of *Escherichia coli*" J Bacteriol. 176(1) 123–129, Jan. 1994.

Bender et al., "Use of a Screen for Synthetic Lethal and Multicopy Suppressee Mutants to Identify Two New Genes Involved in Morphogenesis in *Saccharomyces cerevisiae*," Mol. and Cell. Biol., 11:1295–1305, 1991.

Costigan et al., "NHP6A and NHP6B, Which Encode HMG–1–Like Proteins, Are Candidates for Downstream Components of the Yeast SLT2 Mitogen–Activated Protein Kinase Pathway," Mol. and Cell. Biol. 14:2391–2403, 1994.

Denison et al., "Mutation in the bimD Gene of *Aspergillus nidulans* Confers a Conditional Mitotic Block and Sensitivity to DNA Damaging Agents," Genetics, 134:1085–1096, 1993.

Gietz et al., "Improved method for high efficiency transformation of intact yeast cells," Nucleic Acids Research, 20(6):1425, 1992.

Harris et al., Molecular Analysis of *Saccharomyces cerevisiae* Chromosome I On the Number of Genes and the Identification of Essential Genes Using Temperature–sensitive–lethal Mutations, J. Mol. Biol., 225:53–65 1992

Hooke, "Temperature–Sensitive Mutants of Bacterial Pathogens: Isolation and Use to Determine Host Clearance and in Vivo Replication Rates," Methods in Enzymology, 235:4458–457, 1994.

Karrow et al., "The essential *Escherichia coli* msbA gene, a multicopy suppressor of null mutations in the htrB gene, is related to the universally conserved family of ATP–dependent translocators," Mol. Microbiol., 7(1):69–79, 1993.

Leidich et al., "Temperature–sensitive Yeast GPI Anchoring Mutants gpi2 and gpi3 Are Defective in the Synthesis of – Acetylglucosaminyl Phosphatidylinositol," J. Biol. Chem., 270:13029–13035, 1995.

*Primary Examiner*—Nancy Degen
*Attorney, Agent, or Firm*—Fish & Richardson P.C.

[57] ABSTRACT

A method for identifying a strain having a conditional lethal mutation which is essential for survival when strain is incubated under restrictive growth conditions, and methods of identifying gene products and gene functions thereof.

17 Claims, No Drawings

IDENTIFICATION OF ESSENTIAL SURVIVAL GENES

BACKGROUND OF THE INVENTION

The invention relates to methods of identifying genes and corresponding gene products which are required for survival.

SUMMARY OF THE INVENTION

The invention features a method for identifying a strain carrying a lethal conditional-sensitive mutation in a gene essential for survival. The method includes (a) growing organisms (e.g., cells) under first permissive conditions; (b) exposing organisms from step (a) to restrictive conditions for a period of time equivalent to at least two growth cycles (e.g., cell cycles); and (c) shifting the organisms from step (b) to second permissive conditions for a period of time equivalent to at least ten growth cycles (e.g., cell cycles). Following this treatment, mutant organisms which both (i) failed to grow when exposed to the restrictive conditions of step (b), and (ii) failed to resume growth when returned to the second permissive conditions of step (c) are selected (step (d)).

This selection process separates strains having lethal mutations from strains having nonlethal or static mutations. In general, a selected strain has a gene that is sensitive to the restrictive conditions and that is essential for growth. The transient shift to a restrictive condition results in loss of the gene product; this loss is lethal to the organism. For example, the gene product of the mutated gene is not functional under the restrictive conditions.

Another aspect of the invention features a method for identifying an essential gene in a strain. This method includes (a) growing organisms (e.g., cells) under first permissive conditions; (b) exposing organisms from step (a) to restrictive conditions for a period of time equivalent to at least two cell cycles; (c) shifting the organisms from step (b) to second permissive conditions for a period of time equivalent to at least ten cell cycles; (d) selecting a strain having a lethal mutation, wherein the strain (i) failed to grow when exposed to the restrictive conditions of step (b), and (ii) failed to grow when shifted to the second permissive conditions; (e) identifying a strain selected in step (d) which carries a recessive conditional lethal mutation; and (f) identifying from the strain of step (e) a gene corresponding to the gene encoding the recessive conditional lethal mutation. Preferably, failure to grow is defined by at least three logs of killing, i.e., if 1000 cells are grown under permissive conditions, shifted to restrictive conditions, and then shifted to second permissive conditions, statistically 999 cells are dead. This threshold is intended to identify the more sensitive conditional mutations. Failure to grow can also be defined as 1.5, 2, 3.5, 4, or 5 logs of killing.

Another aspect is a method for identifying a gene product target of a biocidal drug (e.g., antimicrobial, antiparasitic, or insecticidal), including the steps of: (a) growing strains (e.g., fungal, bacterial, parasitic, or insect) under first permissive conditions; (b) exposing the strains from step (a) to restrictive conditions for a period of time equivalent to at least two growth cycles; (c) shifting the strains from step (b) to second permissive conditions for a period of time equivalent to at least ten growth cycles; (d) selecting a strain having a gene carrying a conditional lethal mutation; and (e) identifying the gene product corresponding to the conditional lethal mutation, thereby identifying a gene product target of a biocidal drug.

Once a mutant organism (strain) is identified, routine techniques may be used for transformation, amplification, isolation, purification, and sequencing the gene carrying the mutation. Essential survival genes are required for growth (e.g., metabolism, division, or reproduction). Such genes and gene products are useful in developing therapeutic agents such as antifungal, antibacterial, and antiparasitic agents; insecticidal agents; and preventive antimicrobial agents. Therapeutic agents can reduce or prevent growth, or decrease pathogenicity or virulence, and preferably, kill the organism. The genes and gene products identified by the invention can also be used to develop antimicrobial agents which are effective in preventing microbial infection, e.g., by inhibiting the establishment of a bacterial biofilm, in addition to agents which are useful in the treatment of an established infection.

Other features and advantages of the present invention will be apparent from the following detailed description of the invention, the examples, and also from the appended claims.

DETAILED DESCRIPTION OF THE INVENTION

The invention features a method of identifying mutant organisms having conditional-sensitive lethal mutations, and subsequently gene products thereof. The disclosed methods are useful for high-throughput (e.g., use of 96-well plates) screening of genomic or mutant libraries to rapidly identify genes, and corresponding gene products, which are essential for survival. By altering restrictive conditions, including incubation period, temperature, concentration of an antibiotic, a salt, pH, and so on, and by altering the threshold level of "lethal" (how many logs of killing), the strains can be prioritized.

The selected strains cannot survive under restrictive conditions. The effect of a lethal mutation cannot be reversed or overcome by shifting the organisms to permissive conditions. The selected genes and products thereof are therefore essential for survival of the organism under restrictive conditions. In contrast, strains having nonlethal or static mutations may grow very slowly or even appear inactive under restrictive conditions. The effect of a static mutation is reversible; organisms having static mutations resume metabolism and growth when shifted to permissive conditions. Selection of a conditional-sensitive lethal mutant organism allows identification of the gene carrying the lethal mutation and identification of the corresponding gene product, if any.

A conditional lethal mutation results in a gene or a protein which is not functional under restrictive conditions. A nonfunctional gene can have a defect in the promoter resulting in reduced or abnormal gene expression. A non-functional protein may have a conformational defect causing improper protein folding or abnormal protein degradation. Improper protein folding can result in partial or total failure to fold, to recognize a native substrate, and/or to bind and release the substrate.

Therapeutic agents can be developed from the identification of essential genes of organisms such as bacteria or fungi. Preferably, a gene product (e.g., a protein or an RNA molecule) identified by the methods disclosed herein is distinct from the gene products targeted by existing drugs such as antibiotic or antifungal agents. The disclosed gene selection methods establish that the gene product is essential for survival of the organism. Such an identified gene product therefore serves as a novel target for therapeutics based on a mechanism which is likely distinct from the mechanisms of existing drugs. Similarly, distinct from known compounds is a compound which inhibits the function of a gene product identified by methods disclosed herein, for example, by producing a phenotype or morphology similar to that found in the original mutant strain.

According to one aspect of the invention, a mutant collection is systematically screened to identify genes and preferably gene products which are targets for drugs. For example, an antimicrobial (e.g., antibacterial or antifungal) drug may act as a biocide by binding reversibly, or preferably irreversibly, to the identified gene or gene product target, and thereby impairing its function. Loss of the function (or the synthesis or the complete processing) of the gene product target will result in inhibition of microbial growth, and preferably will result in death of the microbe. This aspect includes a method for identifying biocidal agents, including the step of exposing a gene product corresponding to the wildtype sequence of a mutant sequence identified by methods disclosed herein to the test agent; and selecting agents which impair (preferably, selectively) the function of the gene product. The selection may be based on routinely measured parameters such as a binding constant, dose-response curves or other measurements of inhibition and binding.

In one aspect, the restrictive conditions include a temperature at or near the body temperature of a healthy or infected mammal (e.g., human). In this case, the selected genes are essential for survival of, for example, a fungus at or near the temperature of the human body. In one aspect of the invention, the mutations are temperature sensitive (ts). After identification of a strain carrying the lethal mutation, the location, function, and sequence of the gene and corresponding protein can be determined. Elucidation of the mechanism(s) of action for these targets provides a rational basis for the design of therapeutic agents which are lethal or cidal to the cell used in the method, and related cell types.

In one embodiment of the method for identifying a gene product target of a biocidal drug, the restrictive conditions include changing the temperature and the conditional lethal mutation is a temperature-sensitive mutation or a cold-sensitive mutation. In general, the method is used for large-scale screening, and therefore includes at least 50 or 75 strains, and preferably multiples of 96 strains in steps (a)–(c) through use of 96-well plates.

A. Lethal Mutations

The invention is based, in part, on the recognition that there are at least two types of strains (e.g., cells) which fail to grow under restrictive growth conditions: (a) strains with lethal mutations, and (b) strains with nonlethal or static mutations. In general, strains with lethal mutations are of greater interest for therapeutic research because a bactericidal drug, for example, is generally more desirable than a bacteriostatic drug.

According to the invention, strains carrying lethal mutations must satisfy two criteria. First, when exposed to restrictive conditions for at least two growth cycles, the organism fails to grow. Examples of at least two growth cycles include at least 3, 4, 5, 7, 8, 10 or more growth cycles. Measurements of growth include RNA synthesis, DNA synthesis, protein synthesis, membrane morphology, success of division or reproduction, and levels of ATP. Examples of failure to grow therefore include serious membrane deformity, reduction or absence of DNA (or RNA or protein) synthesis, lysis, ATP depletion, unsuccessful division or reproduction, or even organism death.

The second criterion is that shifting such an organism from restrictive conditions to second permissive growth conditions for a period of time will not revive the organism or restore growth. This organism carries at least one lethal mutation, the product of which is irreversibly sensitive to the restrictive conditions. The gene carrying this mutation is essential for growth during the incubation period under the restrictive conditions.

According to one aspect of the invention, a strain carrying a nonlethal or static mutation is expressly avoided, i.e., not selected. A strain with a nonlethal or static mutation may fail to grow and reproduce under restrictive conditions, and yet will resume growth when shifted from restrictive to second permissive growth conditions. This resumption of substantially normal growth is generally apparent after two or more growth cycles under permissive conditions. In some cases, metabolism or growth may be initially slow during a transition period; in addition, growth may be slower than normal for several growth cycles. In either case, a strain with a static mutation does not satisfy the second criterion for lethal mutation as used herein.

Strains are shifted to the second permissive growth conditions for a period of time sufficient to distinguish the lethal mutations from the static or nonlethal mutations.

The period of time will vary with the method of detecting growth or death, but is generally equivalent to a plurality of growth cycles (e.g., at least 2, 4, 6, 8, 10, 15, or 20 cycles). Depending on the organism and the difference between the restrictive and permissive conditions, growth may be delayed, or the rate of growth may increase during a transition period before stabilizing. Growth can be measured by methods known to those in the art, including expansion of colony cell mass, increased turbidity of a liquid cell culture suspension, cell or organism staining, DNA synthesis, and protein synthesis.

One aspect of the invention provides a method for identifying lethal mutations which produce proteins that are functional at permissive temperatures. Permissive conditions are any conditions under which mutant growth (or growth rate) is at least about 75% of wildtype growth (or growth rate) under the permissive conditions.

In general, under restrictive conditions the wildtype growth rate is not less than about 25%, and preferably not less than about 50%, of the wildtype growth rate under permissive conditions. In bacteria, restrictive conditions include a temperature, wherein the difference between the first permissive and restrictive temperatures is between 5° and 20° C., and preferably between 5° and 15° C. According to the present invention, a temperature sensitive lethal mutation in fungal organisms is a mutation in a gene that is required for fungal growth at temperatures between 5° and 15° C., and preferably between 5° and 12° C., different from a permissive temperature. Once exposed to temperatures several degrees different, (e.g., at least 5, 7, 8 or 10° C. higher or lower) than the permissive temperature (e.g., within a few degrees of optimal growth temperature) for at period at least two cell cycles, a strain with a conditional ts lethal mutation will not resume growth when shifted to permissive conditions.

B. Conditional Mutations

Conditional mutations are mutations wherein the protein cannot function normally (e.g., bind to or release from a substrate) under restrictive conditions. In one aspect, the genes carrying recessive conditional mutations which produce conformational changes in the gene products thereof are preferred as therapeutic targets. This aspect provides a method including the step of selecting a strain carrying a recessive conditional lethal mutation.

Null mutations result in elimination of a gene product, as demonstrated by inability of the strain to survive under restrictive conditions. Dominant lethal mutations produce proteins which can bind a ligand, such as another protein, under restrictive conditions but which are unable to release the ligand. Transformation of a bacterial library of wildtype DNA allows identification of recessive and dominant mutations. Recessive mutations were rescued by a clone which complemented the mutation, and therefore allowed the strain to grow at restrictive temperatures. Strains carrying dominant mutations cannot be rescued by transformation and fail to grow at restrictive temperatures. In fungi, isolation of a diploid or partial diploid organism containing a wildtype allele as well as the lethal mutation allows determination of whether the mutation is recessive or dominant.

C. Prioritization, Complementation, and Gene Function

The disclosed methods efficiently distinguish cells carrying lethal mutations from cells carrying nonlethal or static mutations. Identification of lethal mutations leads, through a variety of paths, to efficient identification of the corresponding genes and gene products. The desired conditional mutations are then mapped and/or sequenced according to any of several methods known to those in the art of molecular biology. Once the strain is selected, conventional methods of transformation, amplification, isolation, and sequencing are used to identify the gene and determine the sequence. Conventional methods are used, preferably, in combination with any of the methods described in the next paragraph or in the Examples.

For example, one embodiment includes the further step of isolating from a selected strain a gene carrying the mutation. Other embodiments include the further step of identifying the function of a gene carrying the mutation, and the further step of sequencing a gene carrying the mutation, respectively.

Where complementation involves DNA having multiple genes, transposon mutagenesis can identify an individual gene which complements the ts mutation (Example 4). Genes can also be prioritized by identifying what gene function or phenotype the mutation affects, such as DNA synthesis, RNA synthesis, protein synthesis, protein secrection, or cell envelope integrity (Example 5). The genes identified by the disclosed methods can be subcloned from plasmid, cosmid, or phage gene libraries by genetic complementation. The disclosed methods are suitable for industrial-scale, high-throughput screening of gene libraries.

D. Organisms

Turning to the first step (a) of growing strains under permissive conditions, in principle, any type of organism or cell which is haploid can be used. Non-haploid organisms susceptible to homozygous mutation (e.g., arabidopsis) can also be used. When speed is desirable, organisms or cells which can be plate cultured are preferred. Organisms can be obtained from a symptomatic or asymptomatic host or from natural environments (e.g., cell colonies growing on decomposed organic material, airborne cells, and cells trapped in ice or found in aqueous solutions). Hosts include plants (e.g., food crops, trees, or fiber crops) and animals, such as mammals (e.g., humans) or domestic animals (horses, cows, pigs, poultry, cats, dogs, mice, rats), birds, fish, and amphibians. Organisms used in the method include bacteria, fungi, yeast, nematodes (e.g., *C. elegans*), protista (e.g., tetrahymena and paramecium), *Rama pipiens*, and *Drosophila* spp.

Bacterial strains include Gram-positive cocci such as *Staphylococcus aureus*, *Streptococcus pyogenes* (group A), *Streptococcus* spp. (viridans group), *Streptococcus agalactiae* (group B), *S. bovis*, *Streptococcus* (anaerobic species), *Streptococcus pneumoniae*, and *Enterococcus* spp.; Gram-negative cocci such as *Neisseria gonorrhoeae*, *Neisseria meningitidis*, and *Branhamella catarrhalis*; Gram-positive bacilli such as *Bacillus anthracis*, *Bacillus subtilis*, *Corynebacterium diphtheriae* and *Corynebacterium* species which are diptheroids (aerobic and anerobic), *Listeria monocytogenes*, *Clostridium tetani*, *Clostridium difficile*, *Escherichia coli*, *Enterobacter* species, *Proteus mirablis* and other spp., *Pseudomonas aeruginosa*, *Klebsiella pneumoniae*, *Salmonella*, *Shigella*, *Serratia*, and *Campylobacter jejuni*. Bacterial infections result in diseases such as bacteremia, pneumonia, meningitis, osteomyelitis, endocarditis, sinusitis, arthritis, urinary tract infections, tetanus, gangrene, colitis, acute gastroenteritis, bronchitis, and a variety of abscesses, nosocomial infections, and opportunistic infections.

Fungal organisms include dermatophytes (e.g., *Microsporum canis* and other *M.* spp.; and *Trichophyton* spp. such as *T. rubrum*, and *T. mentagrophytes*), yeasts (e.g., *Candida albicans*, *C. Tropicalis*, or other *Candida* species), *Saccharomyces cerevisiae*, *Torulopsis glabrata*, *Epidermophyton floccosum*, *Malassezia furfur* (*Pityropsporon orbiculare*, or *P. ovale*), *Cryptococcus neoformans*, *Aspergillus fumigatus*, *Aspergillus nidulans*, and other *Aspergillus* spp., *Zygomycetes* (e.g., *Rhizopus*, *Mucor*), *Paracoccidioides brasiliensis*, *Blastomyces dermatitides*, *Histoplasma capsulatum*, *Coccidioides immitis*, and *Sporothrix schenckii*. Fungal infections (mycoses) may be cutaneous, subcutaneous, or systemic. Superficial mycoses include tinea capitis, tinea corporis, tinea pedis, onychomoycosis, perionychomycosis, pityriasis versicolor, oral thrush, and other candidoses such as vaginal, respiratory tract, biliary, eosophageal, and urinary tract candidoses. Systemic mycoses include systemic and mucocutaneous candidosis, cryptococcosis, aspergillosis, mucormycosis (phycomycosis), paracoccidioidomycosis, North American blastomycosis, histoplasmosis, coccidioidomycosis, and sporotrichosis. Fungal infections also contribute to meningitis and pulmonary or respiratory tract diseases. Opportunistic fungal infections have proliferated, particularly in immunocompromised patients such as those with AIDS. Preferred organisms include *Escherichia coli*, *Streptococcus pneumoniae*, *Staphylococcus aureus*, *Saccharomyces cerevisiae*, *Aspergillus fumigatus*, and *Aspergillus nidulans*. See Goodman and Gilman's *Pharmacological Basis of Therapeutics*, (8th ed., 1990) Table 44-1, page 1024–1033, for additional microbial pathogens, diseases, and current therapeutic agents. The above-described cells are generally available, for example, from the American Type Culture Collection.

E. Mutagenesis

Whatever their source, cells can be mutagenized. Mutagens induce changes in DNA, by acting on one or more bases or by being incorporated into the nucleic acid. In bacteria, the kill rate is preferably 90% (10% or less survive). In yeast and fungi, it is preferable to have a survival rate of 20–50% (e.g., 30%) when mutagenized cells are grown (e.g., replica plated) because cells viable under permissive conditions are necessary for cloning those strains which carry the desired lethal mutations.

Chemical mutagens include ethylmethanesulfonate (EMS), methylmethanesulfonate (MMS), methylnitrosoguanidine (NTG), 4-nitroquinoline-1-oxide (NQO), 2-aminopurine, 5-bromouracil, ICR 191 and other acridine derivatives, sodium bisulfite, ethidium bromide, nitrous acid, hydroxylamine, N-methyl-N'-nitroso-N-nitroguanidine, and alkylating agents. Physical mutagens include ultraviolet radiation and x-rays.

Mutagenesis is accomplished according to methods well-known in the art (see, e.g., *Current Protocols in Molecular*

*Biology* 1995, Vol. 2, Section 13.3, wherein all the cited references are dated 1990 or earlier). Conditions for mutagenesis such as concentration (chemical mutagenesis) or intensity (e.g., ultraviolet mutagenesis) and duration are preferably optimized to produce a high rate of mutation while minimizing the amount of killing among the exposed cells. In general, mutagenesis is performed at a temperature that is below the optimal growing temperature for that type of organism, because the sub-optimal temperature has been found to decrease cell killing. For example, survival curves can be plotted with a constant time of exposure and varying concentrations of mutagen, or a varied time of exposure and a constant concentration of mutagen. See, e.g., Adelberg et al., *Biochem. Biophys. Res. Comm.* 18:788 1965. Kill curves or survival curves are suggestive of mutagenic frequency. Optimum concentrations of nitrosoguanidine have been reported for *Haemophilus influenzae, Salmonella typhi, Escherichia coli, Pseudomonas aeruginosa, Staphylococcus aureus*, and *Listeria monocytogenes* as, respectively, 2, 3, 10, 20, 10–20, and 50 (µg/mL) (see, e.g., Morris Hooke, et al., *Meth. Enzymol.* 34:448, esp. Table I at 451).

F. Permissive and Restrictive Growth Conditions

Growth conditions include temperature, pH, type and concentration of carbon and nitrogen sources, trace minerals, vitamins, salts, cell extracts, proportion of oxygen and carbon dioxide, humidity, presence or absence of conidia-forming materials such as DMSO, glycerol, and deuterated water, and presence or absence of osmotic stabilizers such as sucrose and potassium chloride.

Embodiments of the invention include the following limitations, individually or in combination. Permissive conditions include: a complete medium for the cells to eliminate mutants that are defective in nutritional requirements such as amino acid biosynthesis; and a medium at low osmotic strength to eliminate mutants with defective cell wall or cell surface mutations. In general, permissive conditions should allow strain growth or a growth rate that is at least 75% of that of the wildtype growth or growth rate.

The second permissive conditions can be the same as, or different from, the first permissive conditions. The period of time under the second permissive conditions can be equivalent to at least 2, 5, 10, 15, or 20 growth cycles or more. It is important that the period be long enough to allow organisms carrying irreversible lethal mutations to be distinguished from organisms carrying reversible static mutations. The latter may require time to resume growth after shifting to the second permissive conditions.

Restrictive conditions reduce or arrest growth. Restrictive conditions are non-optimal (above or below optimal) growth conditions. Preferably, restrictive conditions are sufficient to affect the function of mutated genes or gene products. For bacteria, a temperature between 5° and 25° C. (or between 10° and 15° C.) below the optimal growth temperature for wildtype; for fungi, a temperature between 5° and 15° C. (or between 5° and 12° C.) below the optimal growth temperature for wildtype. In general, restrictive conditions for bacteria should result in strain growth that is at least 50% growth or growth rate of the wildtype.

Optimal temperatures are 30° C., 37° C., and 37° C. for *S. cerevisiae, A. nidulans*, and *A. fumigatus*, respectively; sample restrictive temperatures which are higher than optimal growth temperatures are 36° C., 42° C., and 42° C., respectively. The restrictive incubation period should be at least 2 growth cycles in length, and generally not more than 70 growth cycles. For many microbes, the incubation is 3, 4, 5, 7, or 10 cell cycles, but not more than 24 hours.

Restrictive conditions include a temperature between the optimal growth temperature for the cells and 15° C. above the optimal growth temperature for the cells. Restrictive/permissive condition pairs include high/low salt concentrations, high/low temperature, low/high temperature (cryosensitive mutations), high/low osmotic pressure, low/high osmotic pressure, aerobic/anerobic incubation, anerobic/aerobic incubation, glycerol/no glycerol, no DMSO/DMSO, deuterated water/no deuterated water, no deuterated water/deuterated water, low/high pH, and high/low pH.

G. Growth or Failure to Grow Under Restrictive Conditions

According to the invention, the transient disruption of gene function during the period of restrictive growth conditions results in cell death. Organism death can be macroscopically observed in a colony which has the same or reduced size over several growth cycles under the second permissive conditions. Light microscopy and staining can reveal cytological deformations or other morphologies known by those in the art to be indicative of cell death. Under permissive or at least optimal conditions, protein synthesis occurs in a cell which is nominally alive. Dead cells are characterized, in part, by lysis or the absence of DNA, RNA, and protein synthesis.

Note that "temperature sensitive mutants" as used by others includes more than one type of mutant. For example, one type of mutant has a lesion in a gene which is turned on by heat shock and has an essential function turned on during the transition to a restrictive temperature. This type of mutant may survive exposure to temperatures higher than the optimal growth temperature. Another type of ts mutant is affected reversibly by exposure to restrictive temperatures. Neither of these two types is a temperature sensitive lethal mutation. Further guidance is provided by the Examples below.

EXAMPLES

Example 1

Temperature Sensitive *Escherichia coli* Mutants

Log phase *E. coli* cultures (ATCC # K802) were mutagenized in LB medium at 37° C. without aeration. Four incubation treatments were used: (i) EMS (10 µL/mL) for 120 minutes, (ii) NQO (20 µg/mL) for 60 minutes, (iii) NTG (30 µg/mL) for 15 minutes, and (iv) NTG (10 µg/mL) for 30 minutes. After treatment, cells were washed and resuspended in fresh LB medium and grown overnight at 30° C. LB medium consists of 10 g bactotryptone, 10 g sodium chloride, and 5 g yeast extract brought to 1 L with distilled water.

The overnight culture was diluted 100-fold into fresh LB medium and grown at 30° C. to log phase. After ampicillin (100 µg/mL) was added to the log phase culture, the culture was incubated at 42° C. without aeration for 2 hours. Cells were washed and resuspended in fresh LB medium and grown overnight at 30° C.

After $10^7$-fold dilution in LB medium, 100 µL aliquots of culture were spread onto LB agar plates and incubated overnight at 30° C., which is lower than the optimal growth temperature. LB agar plates were prepared with LB medium and 15 g of bactoagar per liter of LB medium.

Each plate (100–200 cfu/plate) was replicated onto another LB agar plate which was then incubated at 42° C. for 7 hours. The master plates were incubated at 30° C. for 7 hours. Colonies which grew well at 30° C. but grew poorly or not at all at 42° C. were struck onto duplicate LB agar plates. The phenotype was confirmed by incubating one duplicate plate at 30° C. and another duplicate plate at 42° C. overnight, and comparing the colonies again. A total of 1500 strains in minimal medium were isolated on LB medium. Twelve genes were isolated and sequenced, one of which has no previously known function. Seventeen genes were isolated and sequenced from screening *Saccharomyces cerevesiae*, two of which have no previously known function.

Example 2
Temperature Sensitive *Aspergillus nidulans* Mutants

*Aspergillus nidulans* (ATCC #FGSC4) were mutagenized following S. D. Harris, et al., Genetics 136:517–532 1994 using 4-nitroquinoline as mutagen.

1150 mutagenized strains were isolated following incubation for 16 hours at 28° C. in minimal medium (MN) medium (pH 6.5, 1% glucose, nitrate salts and trace elements as described in the appendix of Kafer, *Adv. Genet.* 19:33–131, 1977). Trace element solution was stored at 4° C. in the dark; each liter contained 40 mg $Na_2B_4O_7$ (10 $H_2O$), 400 mg cupric sulfate (5 $H_2O$), 1 g ferric phosphate (4 $H_2O$), 600 mg manganese sulfate (4 $H_2O$), 800 mg disodium molybdate (2 $H_2O$), and 8 g zinc sulfate (7 $H_2O$). Salt solution was stored at 4° C. after adding 2 ml chloroform as a preservative; each liter contained 26 g potassium chloride, 26 g magnesium sulfate (7 $H_2O$), 76 g monobasic potassium phosphate and 50 mL trace element solution. Supplement solution is sterilized by autoclaving for 15 minutes and stored in a light-proof container due to reactivity of riboflavin. Each liter contains 100 mg nicotinic acid, 250 mg riboflavin, 200 mg pantothenic acid, 50 mg pyridoxin, 1 mg biotin, and 20 mg p-aminobenzoic acid.

Conidia ($2 \times 10^6$/mL in sterile distilled water) were mutagenized with NQO (4 μg/mL) for 30 minutes at 37° C. with constant shaking. Diluting the conidia with an equal volume of 5% sodium thiosulfate inactivated the NQO. Mutagenized conidia were diluted and plated onto CM+TRITON~ X-100 plates (registered by Union Carbide Chemicals) and incubated at 28° C. for 3 days. Colonies were replica plated and the replica plates were incubated at 28° C. and 42° C. Putative ts mutants were picked and retested, then stored as a colony plug in 15% glycerol at −70° C.

Cells were replica plated and shifted to 42° C. for 24 hours. Strains that grew poorly or not at all were selected. Out of 1150 original strains, 10 did not recover from the 42° C. incubation period.

These 10 strains were transformed with an Aspergillus genomic cos library in pCosAX vector (see Adams and Borgia et al., *FEMS Microbiol. Lett.* 122:227–231 1994. Strains were grown for 3–4 days at 28° C., replica plated and shifted to 42° C. for a maximum of 3 days. Strains which grew were collected; cosmid was recovered from DNA of collected strains. The cosmid was packaged using GIGA-PACK™ III Gold packaging system (Stratagene, La Jolla, Calif.) which produced a plasmid which was isolated, purified, and used to transform bacteria for amplification, isolation, purification, and sequencing. Three genes were isolated and sequenced, two of which are known and one of which has no previously known function.

Example 3
Temperature Sensitive Yeast Mutants

The Abelson library was mildly mutagenized in two sets (A and B) (available from CalTech, Pasadena, Calif.). Set A was SS328 MATα ade2-101 ura3-52 his3 Δ200 lys2-800; set B was SS330 MATα ade2-101 ura3-52 his3 Δ200 tyr1. The Hartwell library was heavily mutagenized (University of Washington); set C was A364a MATα ade-1 ade-2 uro-1 his-7 lys-2 tyr-1 gal(−).

All clones were temperature sensitive and required exogenously supplied uracil for growth. Cells were grown in YPD medium containing 2% peptone, 1% yeast extract, and 2% glucose in 1.8% agar at 26° C. for 2 days. A clone was grown in a microtiter well at 37° C. for 5 hours, then shifted to 26° C. for 16 hours. Cell growth was measured by reading at $OD_{650\ nm}$. After ranking clones according to growth, clones in the lowest 35th percentile were selected. Microscopic examination of these clones resulted in the second round of selection based on irregular or sickly-looking morphology.

Using the master plate as a source, a low-growth clone was grown under osmotic stabilization conditions on YPD medium with 1M sorbitol. Twenty-two out of 99 Abelson clones (22%) were susceptible to sorbitol.

Example 4
Antibacterial Target Genes and Gene Products a. Ts Mutant Isolation Survival curves are prepared using nitrosoguanidine, ethylmethanesulfonate, or hydroxylamine. Temperature-sensitive mutants are isolated on a large scale as follows.

Mutagenize cells and plate survivors at 30° C. Store mutagenized culture. Ts mutants that cannot grow at 42° C. are enriched by selection in the presence of a cell wall-active agent such as ampicillin by shifting culture to 42° C. for 2 hours, and returning cells to 30° C. Cells are replica plated at 42° C. and 30° C. overnight. Test a thick streak of putative ts mutants at 42° C. and 30° C. Streak for single colonies from the 30° C. plate. Store the mutants. Prioritize mutants as discussed in Example 5.

b. Library Construction

Select a vector for cloning wild type DNA of the organism that was mutagenized, and use a shuttle vector if mutagenesis is in an organism other than *E. coli*. The vector may contain a signal element which indicates the presence of an insert, such as a blue-white selection resulting from insertional inactivation of the lacZ gene. Prepare a large wild type chromosomal DNA, such as a SauIIIA1 partial digestion of 5–10 Kb inserts. Pool white transformants into 96-well trays if there are fewer than about 3000 transformants (or scrape plates if more than about 10,000 transformants). Prepare pooled DNA and transform into *E. coli*, and the organism that was mutagenized if other than *E. coli*, such as as *S. aureus*. To assure presence of inserts at a high frequency, prepare 24 minipreps of transformants from both organisms.

c. Complementation of ts Mutants

Transform ts mutants with genome library at 42° C. Include a control plasmid without insert. Pool transformants and prepare DNA to create an enriched pool. Transform with enriched pool at 30° C. Replicate transformants from 30° C. plate onto plates at 42° and 30° C. to identify putative complemented clones. Streak candidates for single colonies from 30° C. plate on plates at 42° and 30° C. Make several (e.g., 5) sequencing grade plasmid preps from complemented clones. Transform the ts mutant, with the sequencing-grade plasmids at 30° C. Streak 5 transformants of each transformation at 42° and 30° C., and compare to control to identify candidates for sequencing.

d. Redundancy of ts Mutants

Redundancy can be monitored by either method described below. For each collection of 10 ts mutants that have been complemented, make a pool of complementing plasmid. Test each pool of 10 against subsequent ts mutants as they are isolated, or as soon as priority is established by a killer ts phenotype. Alternatively, test redundancy within a group of 10 using 90 transformations. Make pools A–E of plasmids that complement mutants 1–10. Pool A contains plasmids complementing mutants 1–5; pool B contains plasmids complementing mutants 6–10; pool C contains plasmids complementing mutants 3–7; pool D contains plasmids 8, 9, 2, and 3; and pool E contains plasmids 1, 4, 6, 8, and 10. The mutants and the corresponding pools for transformation are as follows: 1 (B, C, D); 2 (B, C, E); 3 (B, E) will not detect 2 or 5; 4 (B, D) will not detect 1 or 5; 5 (B, D, E); 6 (A, D) will not detect 7 or 10; 7 (A, D, E); 8 (A, C) will not detect 9 or 10; 9 (A, C, E); and 10 (A, C, D).

e. Transposon Mutagenesis

Transform into donor strain containing gamma-delta on F' but lacking resolvase. Mate transformants into a NalR resolvase+strain selecting for ApR NalR KmR. Prepare pooled DNA and transform the pooled DNA into the ts mutant. Isolate transformants that fail to complement. Prepare sequencing-grade plasmid preps, 2 non-complementing plasmids/ts mutants might be optimal, followed by sequencing.

Tn 1000 mutagenesis using ZK1328 (CBK884) Δ{Δsrl-recA)306::Tn 10Δtet}277/pIF200[pOX38(45 kb HindIII F fragment/conjugation proficient)::myδ-1,Kan)/pXRD4043 (pACYC184-tnpA, cat, IPTG-inducible transposase). The recipient strain is ZK1329(LW49)F⁻recA56,chr::γδ,NAl$^r$. Transform donor strain ZK1328 with complementing plasmid of interest. Select for the antibiotic resistance of incoming plasmid, Cm(40 μg/ml)-resistance and Kan resistance (30 μg/ml). Grow one transformant in 1 ml LB plus 1 mM IPTG at 37° C., no shaking, thereby inducing transposase in the strain and allowing for F-pilus expression. The culture should be grown to $5 \times 10^7$ to $1 \times 10^8$ cells/ml (barely turbid). Concurrently grow 1 ml of the recipient strain ZK1329 in LB to early stationary phase ($2 \times 10^8$ cells/ml). Mix 0.5 ml donor cells with 0.2 ml recipient cells in 50 ml culture tube. Incubate at 37° C. with no shaking for 30 minutes. Add 5 ml prewarmed LB plus 1 mM IPTG, incubate 3 hours at 37°, no shaking. Plate 0.1 ml cells on LB plus 150 μg/ml Amp and 10 μg/ml Nal, thereby selecting against the donor strain. Pool the transconjugants and extract plasmid. There should be about 100 to 1000 transconjugants per plate. Transform original mutant with pool. Check for non-complementing clones (those that do not complement at 42° C.). Isolate plasmid from 2 non-complementing clones and sequence. Tn10 can be used, in the alternative.

Example 5
Prioritization of ts Mutants

By matching an assay to a phenotype under restrictive conditions (e.g., a restrictive temperature), the nature of the mutation can be determined. For example, growing cells at the restrictive temperature for 2, 6, and 24 hours and then shifting to the permissive temperature determines viability after the temperature shift. This considers the irreversibility of the defect; a mutation that results in the loss of viability after a brief shift to the restrictive temperature suggests a gene having an ideal cidal (lethal) target gene product. Monitoring of the optical density of cultures at the restrictive temperature can detect gene products whose loss of function leads to cell lysis. Similarly, microscopic observation can detect filamentation and defects in cell division. Lysis mutants can be examined further for osmotic stabilization. Previously unknown genes which are essential for the integrity or biosynthesis of the cell wall are of great interest.

Precursor labelling studies are also useful. Incorporation of labelled thymine in a short pulse experiment (e.g., 30 minutes, 1 hour, and 6 hours after temperature shift) investigates the arrest of DNA synthesis. In bacteria, incorporation of thymine can be related to incorporation at the permissive temperature; however, incorporation of thymine can be related to incorporation of uracil or of amino acids, all at the restrictive temperature. Similar incorporation (phenotype) pairs include labelled uracil (inhibition of transcription); labelled amino acid (arrest of translation); labelled fatty acid precursor or fatty acid (arrest in membrane biosynthesis); D-alanine for bacteria or glucose in a short pulse for fungi (inhibition of cell wall synthesis).

Susceptibility to antibiotics is another important phenotype. It is useful to obtain a "fingerprint" of resistance to a variety of antibiotics at the permissive temperature and at various temperatures approaching the restrictive temperature. For example, if there is hypersusceptibility to rifampicin, the mutation likely affects transcription. Hypersensitivity to several agents suggests a lesion which affects the cell envelope. Partial resistance to kanamycin may be related to an alteration of the electrochemical gradient. A strain in which the ts lesion is complemented by the wild type DNA on a multi-copy plasmid may result in enhanced resistance to antibiotics when wild type DNA is cloned. In E. coli, transferring a lesion into a secA-lacZ indicator strain suggests blocking secretion. Changes in potassium efflux in bacteria after shifting to the restrictive temperature, possibly in combination with kanamycin resistance, suggests an alteration in the electrochemical gradient, such as collapse of electron potential. Isolation and characterization of temperature-resistant pseudo-revertants of ts mutants suggests mutational suppression. Changes in gene expression at permissive and restrictive temperatures can be shown by 2-D gels, HPLC, or FPLC protein profiles. Total protein and pulse-labelled protein can be detected. Correlation of the changes with a pattern (e.g., shifting cells to medium containing a particular antibiotic) suggests a mutation affecting protein expression.

After isolation of ts mutants, complementation with wild type DNA, and optional prioritization, the DNA sequence and homologies are determined. It is also desirable to identify redundant mutants prior to their complementation by libraries. Redundant ts mutants can be identified by testing for the ability of complementation clones to complement ts mutations in other mutant strains. It is burdensome to test each plasmid that complements one ts mutant for the ability to complement other ts mutants. Where electroporation is used (e.g., S. aureus), an efficient approach can use plasmid pools containing 20 different plasmids. Larger plasmid pools are difficult to prepare due to low transformation frequencies and the reversion frequencies of some ts mutants. It is also desirable to measure growth and microscopically inspect the cells following a temperature shift; perform uptake studies; and other various elaborate studies.

H. Use

The invention features methods of rapidly identifying strains with conditional lethal mutations from a large group of mutants. In general, the gene and corresponding gene product are subsequently identified, although the strains themselves can be used in screening or diagnostic assays. The mechanism(s) of action for the identified genes and gene products provide a rational basis for the design of therapeutic agents which are, for example, lethal against a bacterium used in the method and related species, rather than being merely bacteriostatic.

For example, where the organism used in the method is a fungal or bacterial species, therapeutic agents are antifungal or antibacterial agents. These agents reduce the action of the gene product in a wild type strain, and therefore are useful in treating a subject with that type, or a similarly susceptible type of infection by administering the agent to the subject in a pharmaceutically effective amount. Reduction in the action of the gene product includes competitive inhibition of the gene product for the active site of an enzyme or receptor;

noncompetitive inhibition; disrupting an intracellular cascade path which requires the gene product; binding to the gene product itself, before or after post-translational processing; and acting as a gene product mimetic, thereby down-regulating the activity. Therapeutic agents include monoclonal antibodies raised against the gene product.

Furthermore, the presence of the gene sequence in certain cells (e.g., a pathogenic microbe of the same genus or similar species), and the absence or divergence of the sequence in host cells can be determined. Therapeutic agents directed toward genes or gene products which are not present in the host have obvious advantages including fewer side effects, and lower overall dosage. Enzymatic or ligand binding activity can also be assayed. Other uses include determination of targets for anti-parasitic drugs or insecticides.

OTHER EMBODIMENTS

From the above description, the essential characteristics of the present invention can be easily ascertained. Without departing from the spirit and scope thereof, various changes and modifications of the invention can be made to adapt it to various usages and conditions. Thus, other embodiments are also within the claims.

Examples of other embodiments include a device which performs at least steps (b) and (c), exposing the cells to restrictive conditions and then shifting the cells to the second permissive conditions; and a device which performs at least step (d), optically scanning, staining, or otherwise identifying and selecting cells which failed to grow when shifted to the second permissive conditions.

What is claimed is:

1. A method for identifying a strain carrying a conditional lethal mutation in a gene, the method comprising:

(a) growing strains under first permissive conditions;

(b) exposing strains from step (a) to restrictive conditions for a period of time equivalent to at least two growth cycles;

(c) shifting the strains from step (b) to second permissive conditions for a period of time equivalent to at least ten growth cycles; and (d) selecting a strain that survives step (a) but does not survive steps (b) and (c), thereby identifying a strain carrying a lethal mutation that is sensitive to the restrictive conditions and essential for survival of the strain.

2. A method of claim 1, further comprising after step (d), the step of selecting a strain carrying a recessive conditional lethal mutation.

3. A method of claim 2 in which the strains from step (a) are strains of *Saccharomyces cerevisiae*.

4. A method of claim 1, further comprising after step (d), the step of isolating from said strain a gene carrying said mutation.

5. A method of claim 4, further comprising, after the step of isolating said gene, a step selected from the group consisting of identifying the function of said gene, identifying the product expressed by said gene, and sequencing said gene.

6. A method of claim 1 in which the first permissive conditions include a complete medium for the strains.

7. A method of claim 1 in which the first permissive conditions include a medium at low osmotic strength.

8. A method of claim 1 in which the first permissive conditions include a temperature between 5° and 15° C. below the optimal growth temperature for the wildtype.

9. A method of claim 1 in which the restrictive conditions include a temperature between the optimal growth temperature for the strains and 15° C. above the optimal growth temperature for the strains.

10. A method of claim 1 in which the second permissive conditions are substantially the same as the first permissive conditions.

11. A method of claim 1 in which the strains in growing step (a) are replica plated cells.

12. A method of claim 1 in which the period of time in step (c) is equivalent to at least fifteen growth cycles.

13. A method of claim 1 in which the strains from step (a) are selected from the group consisting of bacteria, fungi, and yeast.

14. A method of claim 13 in which the strains from step (a) are strains of *Escherichia coli, Streptococcus pneumoniae*, or *Staphylococcus aureus*.

15. A method of claim 13 in which the strains from step (a) are strains of *Aspergillus nidulans*.

16. A method of claim 1 in which the strains from step (a) have been mutagenized.

17. A method of claim 16 in which the strains have been mutagenized with a chemical mutagen selected from the group consisting of ethyl methanesulfonate, methyl methanesulfonate, methylnitrosoguanidine, 4-nitroquinoline-1-oxide, 2-aminopurine, 5-bromouracil, ICR 191, acridine derivatives, ethidium bromide, nitrous acid, and N-methyl-N'-nitroso-N-nitroguanidine.

* * * * *